United States Patent [19]

Shippert

[11] Patent Number: 5,401,273

[45] Date of Patent: Mar. 28, 1995

[54] CAUTERIZING INSTRUMENT FOR SURGERY

[76] Inventor: Ronald D. Shippert, 4975 S. Albion St., Littleton, Colo. 80121

[21] Appl. No.: 24,512

[22] Filed: Mar. 1, 1993

[51] Int. Cl.⁶ .............................................. A61B 17/38
[52] U.S. Cl. ...................................... 606/30; 219/236
[58] Field of Search ............... 606/28, 29, 30, 159, 606/40, 49, 31; 607/96, 98, 99, 113; 219/227, 228, 229, 233, 236, 240

[56] References Cited

U.S. PATENT DOCUMENTS

| | | | |
|---|---|---|---|
| 3,234,356 | 2/1966 | Babb | 219/233 |
| 3,295,514 | 1/1967 | Hein et al. | 606/29 |
| 4,367,744 | 1/1983 | Sole | 219/236 |
| 4,563,570 | 1/1986 | Johns | 606/30 |
| 4,869,248 | 9/1989 | Narula | 606/29 |

Primary Examiner—Lee S. Cohen
Assistant Examiner—Brian M. Green
Attorney, Agent, or Firm—Sheridan, Ross & McIntosh

[57] ABSTRACT

An instrument for cauterizing tissue is provided. The instrument includes a housing having an angled member with a free end. A looped cauterizing element is connected to the free end. Power is applied to the cauterizing element using a switching subassembly and a battery power source. The switching subassembly is activatable at a number of portions using a resilient boot to which the surgeon applies pressure to energize the cauterizing element. A copper conductive casing surrounds the battery power source. When the cauterizing instrument is utilized, the angled member enables the instrument to be positioned in a desirable location relative to other instruments used while cauterizing tissue.

24 Claims, 5 Drawing Sheets

CAUTERIZING INSTRUMENT FOR SURGERY

FIELD OF THE INVENTION

The present invention relates to instruments used in performing surgical operations and, more particularly, to a portable cauterizing instrument for applying heat to highly localized portions of the body.

BACKGROUND OF THE INVENTION

In the field of medical surgery, it is known to use instruments for cauterizing tissue of a patient in order to prevent or stop bleeding from blood vessels. One method of cauterizing involves the application of highly localized heat for burning blood vessels causing formation of scar tissue over the exposed blood vessels to prevent bleeding therefrom.

A typical cauterizing instrument comprises a heating element electrically connectable to a power source (e.g., a battery), a switch for selectively completing the circuit between the heating element and the power source, and a housing for enclosing the battery and associated electrical connections. The electrical connections typically comprise one strip of conductive material connecting one end of the heating element to the positive terminal of the power source and another strip of conductive material connecting the other end of the heating element to the negative terminal of the power source with the switch providing a break therebetween. The electrical circuit of the cauterizing instrument is normally open and it does not become a completed circuit unless pressure is applied to a movable member (i.e. a button) on the exterior of the housing to engage the switch. Generally representative of this type of device are U.S. Pat. Nos. 4,359,052 to Staub, issued Nov. 16, 1982; 3,978,312 to Barton et al., issued Aug. 31, 1976; 3,613,682 to Naylor, issued Oct. 19, 1971.

Although a number of cauterizing instruments have been disclosed, it would be advantageous to be able to provide an enhanced cauterizing instrument that meets further worthwhile objectives.

SUMMARY OF THE INVENTION

In accordance with the present invention, a cauterizing instrument is provided for use by a surgeon in connection with cauterizing tissue. The cauterizing instrument includes a housing assembly comprised of a substantially straight body member and a curved angle member. A cauterizing element in the shape of a loop is connected to a free end of the angled member. Activation/deactivation of the cauterizing element is accomplished using an activation assembly. The activation assembly includes a switching subassembly that is disposed intermediate the body member and the angled member. In a preferred embodiment, the switching subassembly can be activated at different portions thereof, with the fingers of the surgeon pushing against a resilient boot to cause conductive contact whereby battery power is applied to the cauterizing element.

In one embodiment, the switching subassembly includes a flanged unit having fingers with conductive strips. When pressure is applied to the boot, at least one of the conductive strips contacts a helical member for completing a circuit path that provides battery power to the cauterizing element. In another embodiment, the switching subassembly includes a ball that is movable to cause a dome to change position. When the dome changes position, a completed circuit path is provided whereby battery power is applied to the cauterizing element.

Batteries that supply the circuit power are preferably enclosed or surrounded by a conductive cover made of copper. The body member is preferably textured to provide an uneven surface for easy gripping and handling of the instrument. The housing parts of the instrument can also be made of different colors to better distinguish the instrument from other surgical instruments and/or the environment in which the instrument may be placed during non-use. The body member preferably also has a base that includes a substantially flat area to desirably locate the cauterizing element when the cauterizing instrument is placed on a support surface.

Based on the foregoing summary, a number of salient features of the present invention are readily seen. A cauterizing instrument is provided that includes a curved section for facilitating positioning of the cauterizing element about, around and under other instruments that might be used during the cauterizing procedure, such as a hemostat. The switching subassemblies of the present invention enable the surgeon to activate the instrument at any one of a number of locations around the resilient boot. A copper conductive casing surrounds the batteries in the instrument housing and provides increased conductivity, as well as reducing batter power consumption. Relatedly, a smaller size cauterizing element is utilized to also reduce battery power usage and enable the cauterizing element to be used in more closely confined spaces.

Additional advantages of the present invention will become readily apparent from the following discussion, particularly when taken in conjunction with the accompanying drawings.

DETAILED DESCRIPTION

FIGS. 1-9 illustrate a cauterizing instrument 20 embodying the present invention. The cauterizing instrument 20 generally comprises a housing assembly 30, a cauterizing assembly 70, and an activating assembly 100.

Figure 7:
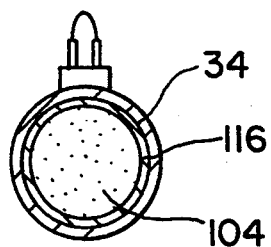
FIG. 7 is a sectional view taken along line 7—7 of FIG. 4 illustrating the copper conductive cover surrounding a battery.
Figure 8:
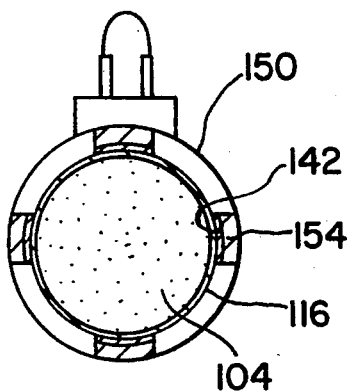
FIG. 8 is a sectional view taken along line 8—8 of FIG. 4 illustrating the finger portions of the flanged unit.

The housing assembly 30 of the present embodiment comprises a body member 34 and an angled member 62. The body member 34 is preferably a hollow, cylindrically-shaped member having an open end 38, a closed end 42, a central axis 46 and a substantially circular cross-section, as shown in FIGS. 7 and 8. However, the body member may comprise a variety of different shapes (e.g., triangular, square, oval, or with finger ridges) without detracting from the present invention. The outer surface 50 of the body member 34 is textured, or roughened, to enhance the gripping characteristics of the instrument. The body member 34 is further designed to receive a power source 104 (e.g., batteries) therein, as described herein in more detail.

Figure 3:
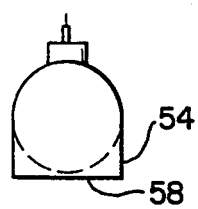
FIG. 3 is an end elevational view thereof illustrating the base having a flattened area.

The body member 34 comprises a base 54 positioned on the closed end 42 of the body member 34. The base 54 has an irregularly shaped (e.g., non-circular) cross-section to prevent the cauterizing instrument 20 from rolling when it is placed on a flat surface. The irregularly shaped cross-section may comprise a flattened surface 58 on one side of the base 54 as shown in FIG. 3. The base 54 is preferably designed such that, when the cauterizing instrument 20 is placed on a surface with the cauterizing element 74 facing upwards, the irregular shape of the base 54 substantially prevents the cauterizing instrument 20 from rolling and potentially burning something or someone with the element. It should be appreciated that the base 54 could be positioned at any location along the housing assembly 30 and, preferably, could be integrated with the body member 34 or angled member 62 as a unitary component.

Figure 1:
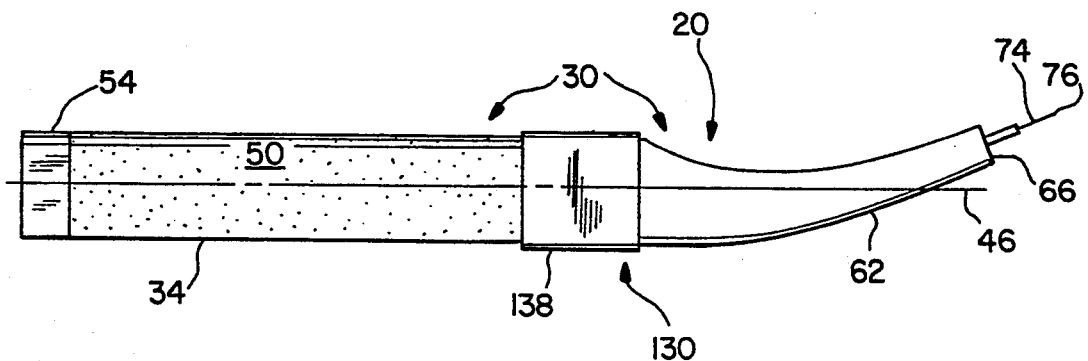
FIG. 1 is a side elevational view of the cauterizing instrument of the present invention.
Figure 4:
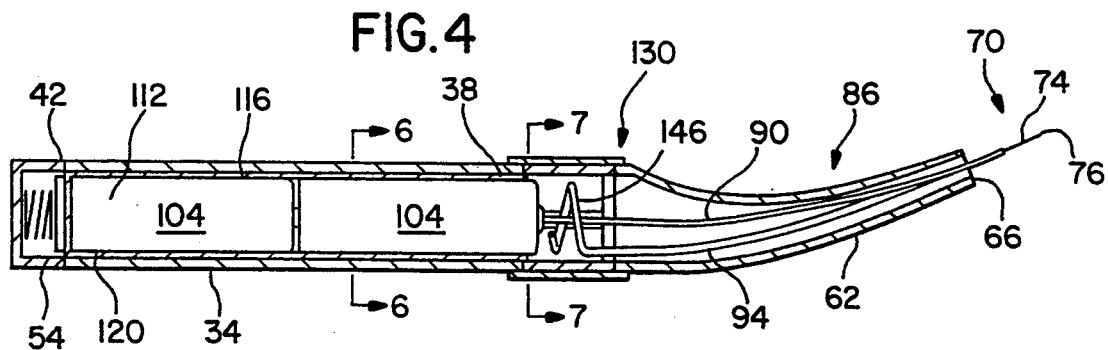
FIG. 4 is a side sectional view illustrating the assemblies of the present invention.

The angled member 62 of the housing assembly 30 extends from the end of the switching subassembly 130 opposite the body member 34. The angled member 62 is preferably made of a color different from the color of the body member 34. At least part of the angled member 62 is at an angle to the central axis 46 of the body member 34. The angled member 62 of the present embodiment is preferably gradually curved and tapered from the switching subassembly 130 to a free end 66 of the angled member 62. The free end 66 is consequently at an angle to and is offset from the central axis 46 of the body member 34, as shown in FIGS. 1 and 4. The curve of the angled member 62 is preferably defined by a radius having a magnitude that is a function of the length of the body member 34, the angle at which the cauterizing instrument 20 is commonly held while being used to cauterize tissue, and the capability of avoiding other instruments during cauterizing. It should be appreciated that the angled member 62 could be straight (e.g., at an angle, but not curved) and not tapered without detracting from the present invention. In addition, the angled member 62 could project away from the central axis 46 of the body member and then back towards the central axis 46 (e.g., in a "U" or "V" shape) such that the cauterizing element 74 is positioned in line with the central axis 46 of the body member 34.

Figure 2:
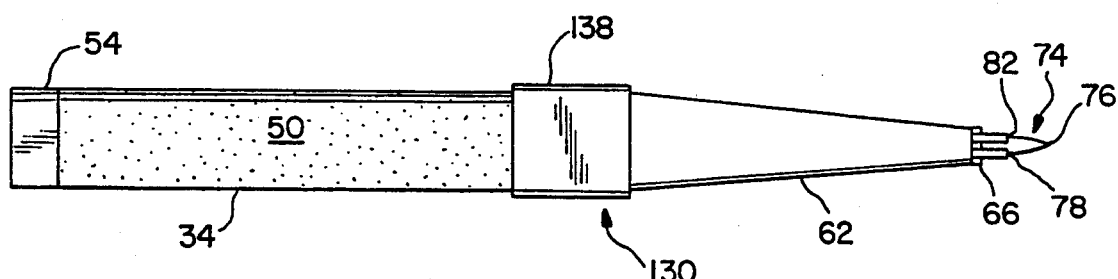
FIG. 2 is a top plan view thereof.

The cauterizing assembly 70 comprises a cauterizing element 74 having first and second ends 78, 82, with a tip 76. The tip 76, as seen in FIG. 1, is located at a distance outwardly from the body member 34 such that, if the length of the body member 34 were extended, such an extension would not intersect the tip 76. The cauterizing assembly also includes an electrical interconnect subassembly 86 for electrically connecting the first and second ends 78, 82 to the power source 104. The electrical interconnect subassembly 86 preferably comprises first and second electrical current conductors 90, 94 for electrically connecting the first end 78 of the cauterizing element 74 to the positive terminal 108 of the power source 104 and the second end 82 of the cauterizing element 74 to the switching subassembly 130, respectively. The conductors 90, 94 are positioned within the angled member 62 and extend through, and partially beyond, the free end 66 of the angled member 62. The conductors 90, 94 of the present invention may be hollow brass tubes and each end 78, 82 of the cauterizing element 74 may preferably be inserted into the respective brass tubes and secured (e.g. by crimping the ends of the tubes) thereto. As seen in FIG. 2, the cauterizing element 74 is preferably in the shape of a loop terminating in the ends 78, 82. In contrast to prior cauterizing element loops, the loop of the present invention is substantially smaller in size. The length of the loop is less than about 0.20 inch and the width is less than about 0.13 inch, with the loop height preferably being about 0.16 inch and the loop width being about 0.12 inch. The smaller size loop reduces battery power consumption and better allows the surgeon to cauterize in more closely confined spaces.

The activating assembly 100 provides interruptable current to the cauterizing assembly 70 and is essentially located between the body member 34 and the angled member 62. The activating assembly 100 comprises a power source 104 (e.g., batteries) having a positive terminal 108 and a negative terminal 112, a conductive cover 116, a spring 120, a movable partition 124, and a switching subassembly 130. The power source 104 is encased by the conductive cover 116 which is electrically interconnected to the negative terminal 112 of the power source 104. The conductive cover 116 is cylindrically shaped and extends inside of the body member 34 from the closed end 42 to the open end 38. The conductive cover 116 is made substantially entirely of copper, instead of brass, to provide greater conductivity since the resistance is lessened and also results in conserving battery power. The spring 120 is positioned adjacent the interior of the closed end 42 of the body member 34 and applies a compressive force on the conductive cover 116 through the movable partition 124 to maintain the power source 104 in a relatively compressed and rigid condition. As previously discussed, the positive terminal 108 of the power source 104 is electrically interconnected with the first end 78 of the cauterizing element 74 by the first conductor 90. The conductive cover 116, which is electrically interconnected to the negative terminal 112 of the power 104 source, is further electrically interconnected with the switching subassembly 130 through the conductive strips 142 as described herein in more detail.

Figure 5A:
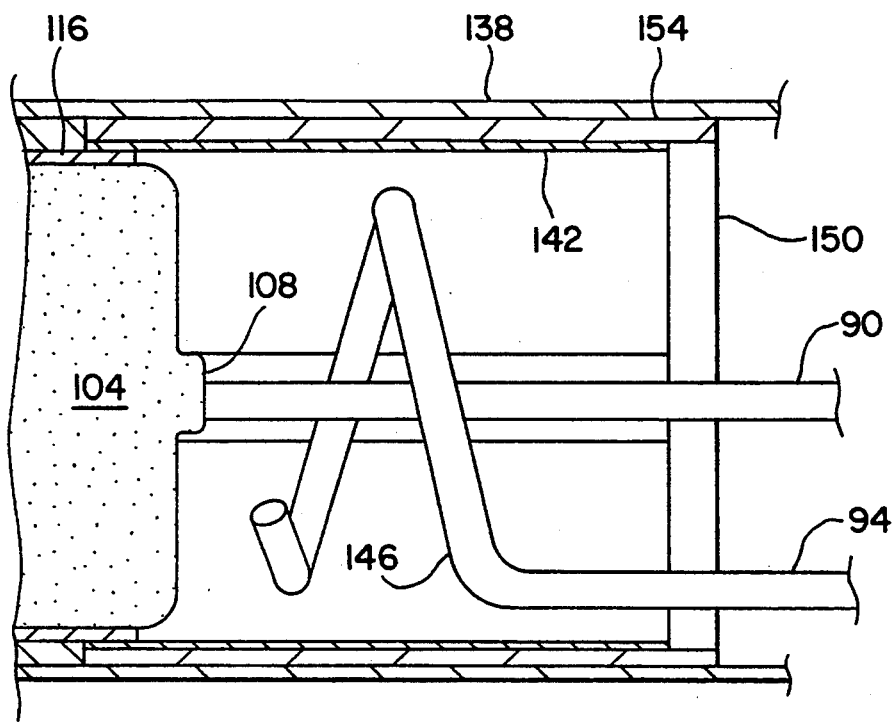
FIG. 5A is an enlarged side sectional view of one embodiment of a switching subassembly.
Figure 9:
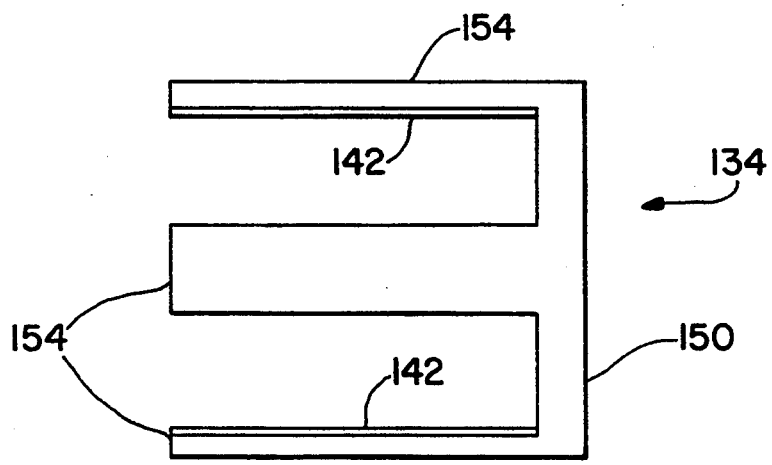
FIG. 9 is a side view of the flanged unit.

The switching subassembly 130 of the present embodiment selectively activates and deactivates the cauterizing assembly 70 by connecting and disconnecting the circuit. The switching subassembly 130 generally comprises a flanged unit 134, a flexible boot 138, a plurality of conductive strips 142, and a helical member 146. The flanged unit 134 comprises a sleeve portion 150 and a plurality of finger portions 154 extending therefrom. The conductive strips 142 are mounted on the interior surface of each finger portion 154 of the flanged unit 134, as shown in FIG. 9. The flanged unit 134 is positioned between the body member 34 and the angled member 62 of the housing assembly 30 and is situated such that the conductive strips 142 touch, and are thus electrically interconnected with, the conductive cover 116, as shown in FIG. 5A.

Figure 6:
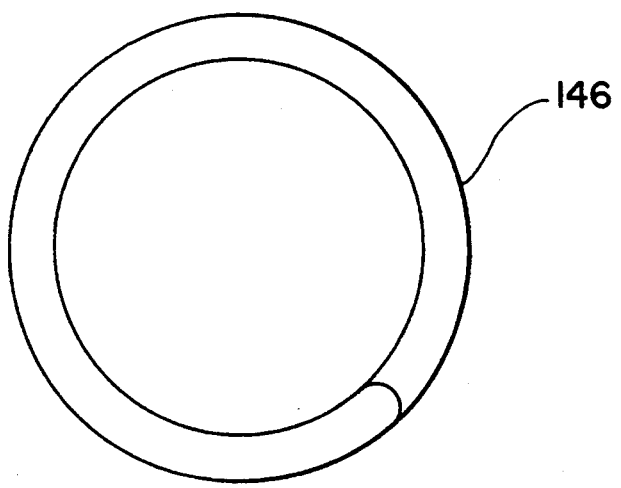
FIG. 6 is an enlarged front view of the helical member of the switching subassembly illustrating its generally circular cross-section.

The helical member 146 is an extension of the second conductor 94 and is positioned between, but not in contact with, the plurality of conductive strips 142. Because of its circular cross-section, as seen in FIG. 6, the helical member 146 maintains a substantially equal distance from each of the plurality of conductive strips 142 when the switching subassembly 130 is deactivated. It should be appreciated that the helical member 146 could comprise other shapes (e.g. disk, annular, rectangular, triangular, etc.) without detracting from the invention.

The flexible boot 138 is cylindrically-shaped and encases the flanged unit 134. The flexible boot 138 extends slightly beyond the flanged unit 134 on both ends thereof to partially cover the body member 34 and angled member 62 to provide a substantially fluid-resistant barrier between the flanged unit 134 and the exterior environment.

Figure 5B:
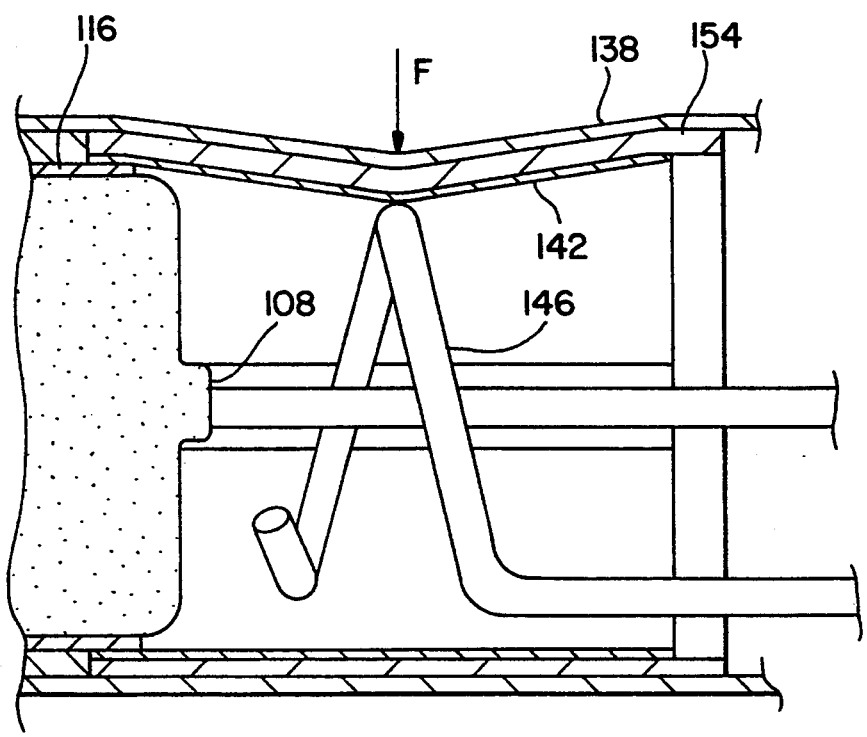
FIG. 5B is an enlarged side sectional view similar to FIG. 5A but illustrating activation of this switching subassembly.
Figure 11:
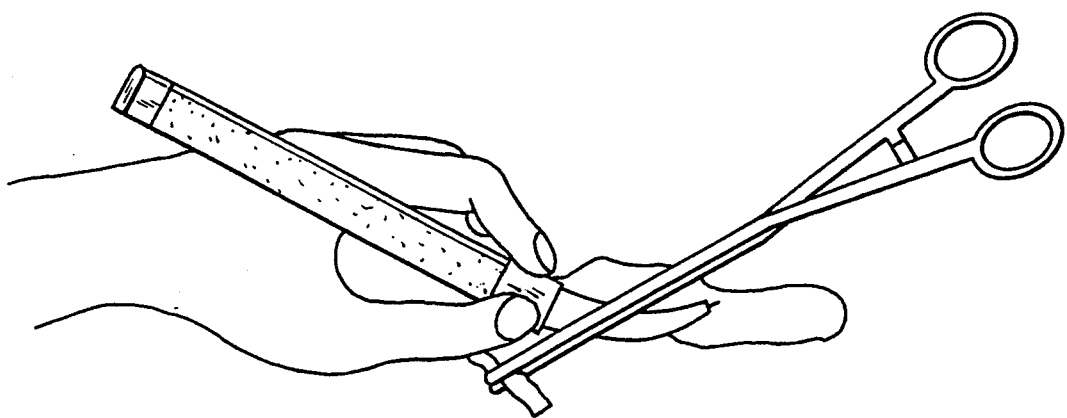
FIG. 11 is a diagrammatic view representing use of the cauterizing instrument in which the angled member is located under another instrument.
Figure 12:
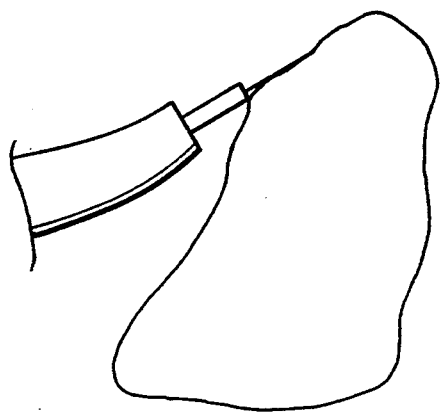
FIG. 12 is an enlarged diagrammatic view representing the parallel position of the cauterizing element loop during use.

In operation, the cauterizing instrument 20 is held by the user such that the user's thumb and forefinger are on opposing sides of the flexible boot, as shown in FIG. 11. When heat is desired in the cauterizing element 74, the user applies pressure to at least one point on the exterior surface of the flexible boot 138, thus causing deflection of at least one of the plurality of finger portions 154 of the flanged unit 134, as shown in FIG. 5B. When at least one finger portion 154 has been deflected a sufficient amount, the corresponding conductive strip 142 on the interior surface of the finger portion 154 will contact the helical member 146 to provide an electrical connection between the helical member 146 and the conductive cover 116. This electrical connection completes the circuit to provide current to the cauterizing element 74, causing it to heat. Upon removal of pressure to the exterior of the flexible boot 138, the finger portion 154 straightens and the electrical connection is broken, as shown in FIG. 5A, thus stopping the flow of current to the cauterizing element 74. With reference to FIG. 12, a further feature of the cauterizing element 74 is represented. During operation, the cauterizing element 74 remains virtually parallel to the free end 66 of the angled member 62. As a consequence, more surface area of the cauterizing element 74, i.e., substantially the entire loop, is used in applying heat to the tissue to be cauterized. This is in contrast to prior art loops that are bent at an angle relative to the ends to which they are connected. In such a case, substantially only the tip of the cauterizing element is available for conducting the cauterizing step.

It should be appreciated that, because the plurality of finger portions 154 are spaced circumferentially about the helical member 146, the pressure applied by the user could be applied at any of a number of circumferential locations on the exterior surface of the flexible boot 138. This feature accommodates the handling of the instrument 20 in a variety of positions. In addition, due to the angling of the angled member 62 with respect to the central axis 46 of the body member 34, the present invention provides a cauterizing instrument 20 that can be used to reach around other objects or instruments to cauterize difficult to reach locations. Moreover, by providing an irregularly shaped base 54, the present invention provides a cauterizing instrument 20 capable of being placed on a flat surface without rolling over. Furthermore, the use of a cylindrically-shaped conductive cover 116 made of copper to connect the negative terminal 112 to the switching subassembly 130 provides a low resistance pathway for the current to follow, thus extending the life of the power source 104 and/or providing more power to the cauterizing element 74.

Figure 10A:
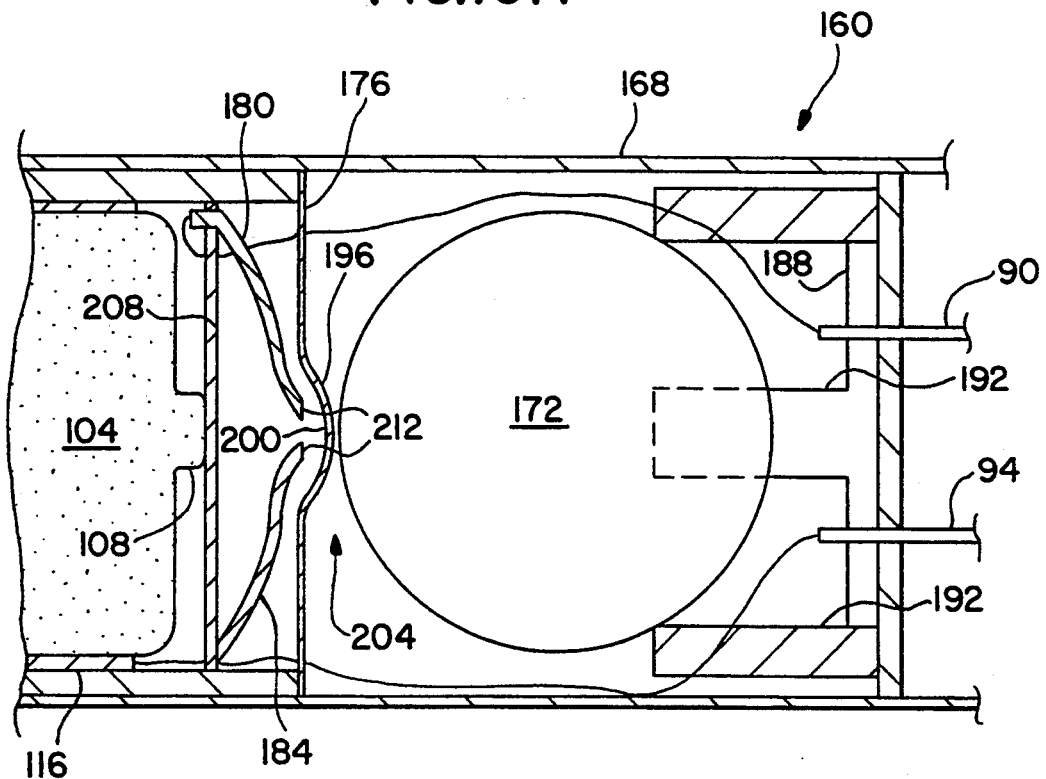
FIG. 10A is an enlarged side sectional view of an alternative embodiment of the switching subassembly.

In an alternative embodiment of the cauterizing instrument 20, the switching subassembly 130 is of the "snap dome" type as shown in FIG. 10A. The snap dome switch 160 generally comprises a flanged unit 164, a flexible boot 168, a ball 172, a dome 176, and first and second wires 180, 184. The flange unit 164 comprises a sleeve portion 188 and a plurality of finger portions 192 extending therefrom. The flanged unit 164 is positioned between the body member 34 and the angled member 62 and is situated such that the finger portions 192 extend from the sleeve portion 188 toward the body member 34.

The ball 172 is positioned adjacent to and partially between the finger portions 192 such that the finger portions 192 contact at least part of the ball 172. The ball 172 is not rigidly attached to any other part of the switch and is free to move under the various forces applied to it. The dome 176 is mounted on the body member 34 and is positioned such that the convex side 196 of the dome 176 is adjacent to the ball 172. At least part of the dome 176 (e.g., a central portion 204) is constructed from a conductive material. The dome 176 is designed such that the central portion 204 will invert (i.e., the convex side 196 will become concave and the concave side 200 will become convex) upon application of a sufficient force to the convex side 196 and will return to its original position upon removal of the force. The inversion of the central portion 204 results in a "clicking" sensation being felt and/or heard by the user of the cauterizing instrument 20.

Adjacent the concave side 200 of the dome 176, there is positioned the first and second wires 180, 184. The first wire 180 is electrically interconnected with the first conductor 90 and the second wire 184 is electrically interconnected with the positive terminal 108 of the power source 104 (e.g. through a conductive mount 208). It should also be noted that the second conductor 94 of this embodiment is electrically interconnected with the negative terminal 112 of the power source 104 via the conductive cover 116. Thus, it can be appreciated that the circuit is open between the first and second wires 180, 184. The tips 212 of the first and second wires 180, 184 are positioned such that, when the central portion 204 of the dome 176 inverts, the conductive material of the central portion 204 provides an electrical connection between the first and second wires 180, 184 and completes the circuit. The flexible boat 168 of this alternative embodiment is substantially similar to, and performs the same functions as the flexible boot of the previous embodiment.

Figure 10B:
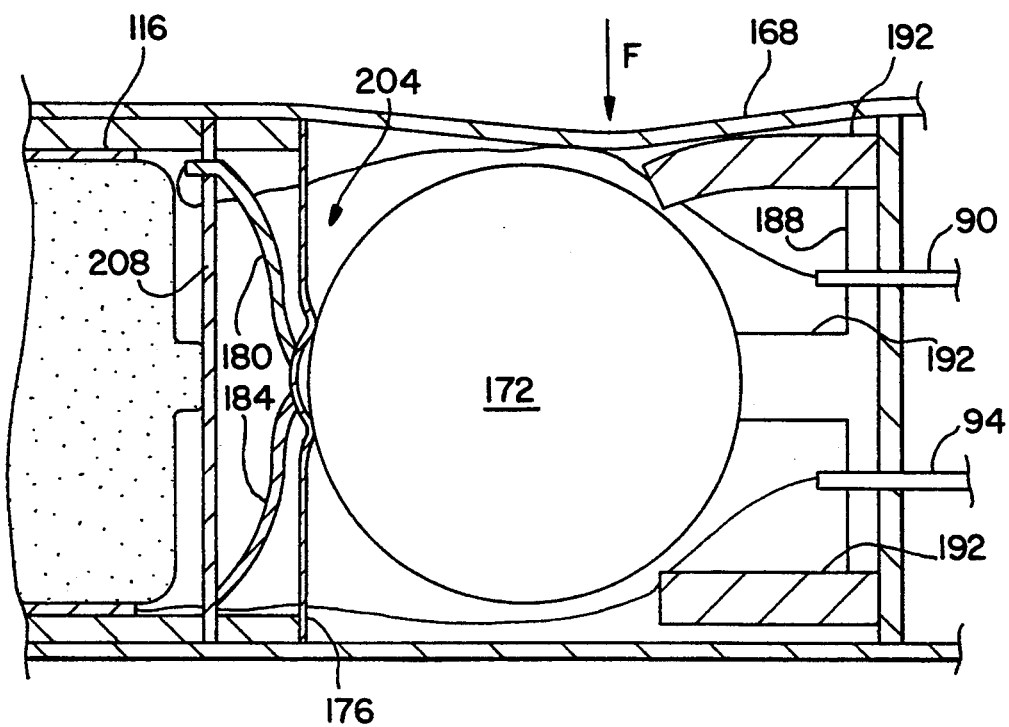
FIG. 10B is an enlarged side sectional view similar to FIG. 10A but illustrating activation of this switching subassembly.

In operation, similar to the previous embodiment, the cauterizing instrument 20 is held by the user such that the user's thumb and forefinger are on opposing sides of the flexible boot 168, as shown in FIG. 11. When heat is desired in the cauterizing element 74, the user applies pressure to at least one point on the exterior surface of the flexible boot 168, thus causing deflection of at least one of the plurality of finger portion 192 of the flanged unit 164, as shown in FIG. 10B. Deflection of a finger portion 192 causes the ball 172 to be forced away from the flanged unit 164 to put force on the central portion 204 of the dome 176. When a sufficient force has been applied, the central portion 204 will invert, resulting in a "clicking" sensation to the user of the cauterizing instrument 20. The inverted central portion 204 provides an electrical connection between the first and second wires 180, 184, thus resulting in a completed circuit. The central portion 204 will remain inverted until pressure is released from the exterior surface of the flexible boot 168.

The foregoing discussion of the invention has been presented for purposes of illustration and description. Further, the description is not intended to limit the invention to the form disclosed herein. Consequently, variations and modifications commensurate with the above teachings, and the skill or knowledge in the relevant art, are within the scope of the present invention. The embodiments described hereinabove are further intended to explain modes known of practicing the invention and to enable others skilled in the art to utilize the invention in such, or other, embodiments and with the various modifications required by their particular applications or uses of the invention. It is intended that the appended claims be construed to include alternative embodiments to the extent permitted by the prior art.

What is claimed is:

1. A cauterizing instrument used in surgery to cauterize tissue, comprising:
    housing means for providing an exterior shape of said cauterizing instrument, said housing means including a body member having a body end terminating a length of said body member along a longitudinal axis thereof and further including an angled member having a free end, said angled member extending from said body end in at least one direction different from said longitudinal axis so that said angled member includes a curved section;
    cauterizing means including a cauterizing element extending from said angled member for providing cauterizing heat to tissue; and
    activating means for selectively activating and deactivating said cauterizing instrument, wherein said curved section begins adjacent to said activating means.

2. A cauterizing instrument used in surgery to cauterize tissue, comprising:
    housing means for providing an exterior shape of said cauterizing instrument, said housing means including a body member having a body end terminating a length of said body member along a longitudinal axis and further including an angled member having a free end, said angled member extending from said body end in at least one direction different from said longitudinal axis;
    cauterizing means including a cauterizing element extending from said angled member for providing cauterizing heat to tissue and said cauterizing element has a tip that is located at a distance outwardly from said body member and in which any extended length of said body member does not intersect said tip; and
    activating means, located on said housing means, for selectively activating and deactivating said cauterizing instrument.

3. A cauterizing instrument used in surgery to cauterize tissue, comprising:
    housing means for providing an exterior shape of said cauterizing instrument, said housing means including a body member having a body end terminating a length of said body member along a longitudinal axis and further including an angled member having a free end, said angled member extending from said body end in at least one direction different from said longitudinal axis so that said angled member includes a curved section;
    cauterizing means including a cauterizing element extending from said angled member for providing cauterizing heat to tissue; and
    activating means for selectively activating and deactivating said cauterizing instrument;
    wherein said curved section is defined by a radius having a magnitude with said magnitude being a function of a length of said body member, an angle at which said cauterizing instrument is held while being used to cauterize the tissue and being able to position said cauterizing element to avoid other instruments during use of said cauterizing instrument.

4. An instrument, as claimed in claim 3, wherein: said angled member has a different color from said body member.

5. An instrument, as claimed in claim 3, wherein: said body member includes an uneven outer surface.

6. An instrument, as claimed in claim 3, wherein:
    said cauterizing element has a loop shape with a length less than about 0.20 inch and a width less than about 0.13 inch.

7. An instrument, as claimed in claim 6, wherein:
    said loop shape having a length of about 0.16 inch and having a width of about 0.12 inch.

8. An instrument, as claimed in claim 3, wherein: said curved section tapers from said body member to said free end.

9. A cauterizing instrument used in surgery to cauterize tissue, comprising:
    housing means for providing an exterior shape of said cauterizing instrument, said housing means including a body member having a body end terminating a length of said body member along a longitudinal axis and further including an angled member having a free end, said angled member extending from said body end in at least one direction different from said longitudinal axis;
    cauterizing means including a cauterizing element extending from said angled member for providing cauterizing heat to tissue, wherein said body member includes a base having a substantially flat area, said flat area being disposed such that said flat area and said cauterizing element face substantially opposite directions; and
    activating means for selectively activating and deactivating said cauterizing instrument.

10. A cauterizing instrument used in surgery to cauterize tissue, comprising:
    housing means for providing an exterior shape of said cauterizing instrument, said housing means including a body member having a body end terminating a length of said body member along a longitudinal axis and further including an angled member having a free end, said angled member extending from said body end in at least one direction different from said longitudinal axis;

cauterizing means including a cauterizing element extending from said angled member for providing cauterizing heat to tissue; and activating means, located on said housing means, for selectively activating and deactivating said cauterizing element, said activating means includes switch means for activating/deactivating said cauterizing element at any one of a plurality of positions.

11. An instrument, as claimed in claim 10, wherein: said plurality of positions extends about a perimeter of said cauterizing instrument subtending an angle of at least 180 degrees.

12. An instrument, as claimed in claim 10, wherein: said switch means includes a movable element so that when said switch is one of activated and deactivated, said movable element changes shape providing at least one of auditory and touch feedback.

13. A cauterizing instrument used in surgery to cauterize tissue, comprising:

housing means for providing an exterior shape of said cauterizing instrument, said housing means including a body member having a body end terminating a length of said body member along a longitudinal axis and further including an angled member having a free end, said angled member extending from said body end in at least one direction different from said longitudinal axis;

cauterizing means including a cauterizing element extending from said angled member for providing cauterizing heat to tissue; and activating means, located on said housing means, for selectively activating and deactivating said cauterizing element, said activating means includes switch means for activating/deactivating said cauterizing element at any one of a plurality of positions;

wherein said switch means includes a flanged unit having a number of spaced fingers in which a change in position of at least one of said fingers causes a change in state of said switch means.

14. An instrument, as claimed in claim 13, wherein: said switch means includes a boot disposed about said flanged unit, said boot being located between said angled member and said body member, said boot being made of a resilient material.

15. An instrument, as claimed in claim 13, wherein: each of said number of spaced fingers has a strip of conductive material connected to a surface thereof.

16. An instrument, as claimed in claim 15, wherein: said cauterizing means includes a first conducting wire and a second conducting wire with each of said first and second conducting wires being connected to said cauterizing element, said first conducting wire being electrically connectable to at least one of said strips of conductive material when said switch means is activated.

17. An instrument, as claimed in claim 13, wherein: said cauterizing means includes a first conducting wire and a second conducting wire with each of said first and second conducting wires being connected to said cauterizing element, said first conducting wire being electrically connectable to said activating means to complete a circuit path, wherein said switch means includes a movable member for completing the circuit path between said first conducting wire and said activating means when said switch means is activated.

18. An instrument, as claimed in claim 17, wherein: said switch means outputs one of a sound and a touch sense change when activated/deactivated.

19. A cauterizing instrument used in surgery to cauterize tissue, comprising:

cauterizing means including a cauterizing element for providing cauterizing heat to issue;

activating means for selectively activating and deactivating said cauterizing element, said activating means including a battery and conductor means for reducing resistance in a circuit path, said conductor means contacting at least a negative terminal of said battery; and a housing containing said battery and with said conductor means being separate from said housing and being made of copper and said cauterizing element extending from said housing;

wherein said conductor means substantially surrounds said battery including a length of said battery.

20. A method for cauterizing tissue, comprising:

providing a cauterizing instrument having a housing that includes a curved section and a cauterizing element connected to a free end of said curved section;

positioning said cauterizing element adjacent to an area to be cauterized; and activating said cauterizing element using at least one of a plurality of portions on said housing to cauterize the tissue.

21. A method, as claimed in claim 20, wherein: said positioning step includes inserting said curved section under another instrument.

22. A method, as claimed in claim 20, wherein: said providing step includes maintaining said cauterizing element substantially parallel to said free end of said curved section.

23. A method, as claimed in claim 20, wherein: said positioning step includes locating substantially all of said cauterizing element substantially parallel to the tissue to be cauterized.

24. A cauterizing instrument used in surgery to cauterize tissue, comprising:

housing means for providing an exterior shape of said cauterizing instrument, said housing means including a body member having a body end terminating a length of said body member along a longitudinal axis and further including an angled member having a free end, said angled member extending from said body in at least one direction different from said longitudinal axis;

cauterizing means including a cauterizing element extending from said angled member for providing cauterizing heat to tissue; and activating means for selectively activating and deactivating said cauterizing element, said activating means includes switch means for activating/deactivating said cauterizing element at any one of a plurality of positions, said switch means including:

(a) a flanged unit having a number of spaced fingers in which a change in position of at least one of said fingers causes a change in state of said switch means;

(b) a circular unit inward of said spaced fingers wherein an inwardly directed force applied to a first finger of said spaced fingers results in said circular unit contacting an element of said switch means at a point on said circular unit not contacted when the inward force is not applied, the contacting point is used in providing a cauterizing current when the inward force is applied.

* * * * *